US010995059B2

(12) United States Patent
Sommadossi et al.

(10) Patent No.: US 10,995,059 B2
(45) Date of Patent: May 4, 2021

(54) CRYSTALLINE EPINEPHRINE MALONATE SALT

(71) Applicant: Biothea Pharma, Inc., Boston, MA (US)

(72) Inventors: Jean-Pierre Sommadossi, Boston, MA (US); Adel Moussa, Burlington, MA (US)

(73) Assignee: Biothea Pharma, Inc., Boston, MA (US)

( * ) Notice: Subject to any disclaimer, the term of this patent is extended or adjusted under 35 U.S.C. 154(b) by 0 days.

(21) Appl. No.: 16/526,286

(22) Filed: Jul. 30, 2019

(65) Prior Publication Data

US 2020/0031758 A1 Jan. 30, 2020

Related U.S. Application Data

(60) Provisional application No. 62/731,442, filed on Sep. 14, 2018, provisional application No. 62/711,936, filed on Jul. 30, 2018.

(51) Int. Cl.
| | |
|---|---|
| *C07C 215/60* | (2006.01) |
| *A61K 47/12* | (2006.01) |
| *A61K 47/10* | (2017.01) |
| *A61K 47/38* | (2006.01) |
| *A61K 47/32* | (2006.01) |
| *A61K 47/02* | (2006.01) |

(52) U.S. Cl.
CPC ............ *C07C 215/60* (2013.01); *A61K 47/02* (2013.01); *A61K 47/10* (2013.01); *A61K 47/12* (2013.01); *A61K 47/32* (2013.01); *A61K 47/38* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 2,332,075 | A | 10/1943 | Gustus |
| 2,469,967 | A | 5/1949 | Kaiser et al. |
| 2,602,818 | A | 7/1952 | Tendick et al. |
| 2001/0033866 | A1 | 10/2001 | Ogorka et al. |
| 2007/0059361 | A1 | 3/2007 | Rawas-Qalaji et al. |
| 2011/0237681 | A1 | 9/2011 | Batycky et al. |
| 2017/0196896 | A1* | 7/2017 | Bologna ................. A61P 35/00 |
| 2017/0216199 | A1 | 8/2017 | Potta et al. |

FOREIGN PATENT DOCUMENTS

| | | |
|---|---|---|
| WO | 2009004593 A2 | 1/2009 |
| WO | 2015054359 A1 | 4/2015 |

OTHER PUBLICATIONS

Bose, et al. "Observations on the pharmacological activity of different salts of adrenaline, morphine and strychnine" Indian J Med Res. 46(2):193-8 (Mar. 1958).
John J. Sciarra, et al. "Synthesis and Formulation of Several Epinephrine Salts as an Aerosol Dosage Form" Journal of Pharmaceutical Sciences, 61(2), 219-223 (1972).
K. J. Simons, et al. "Sublingual Epinephrine Administration in Humans: A Preliminary Study" S260 Abstracts, J Allergy Clin Immunol, Feb. 2004, 1 page.
Mutasem M. Rawas-Qalaji, et al. "Sublingual epinephrine tablets versus intramuscular injection of epinephrine: Dose equivalence for potential treatment of anaphylaxis" J Allergy Clin Immunol, vol. 117, No. 2, Feb. 2006, pp. 398-403.
Tom E. Peddicord, et al. "Stability of high concentration dopamine hydrochloride, norepinephrine bitartrate, epinephrine hydrochloride, and nitroglycerin in 5% dextrose injection," Am J Health-Sys Pharm. 1997, vol. 54, pp. 1417-1419.
Mutasem M. Rawas-Qalaji, et al. "Epinephrine for the treatment of anaphylaxis: Do all 40 mg sublingual epinephrine tablet formulations with similar in vitro characteristics have the same bioavailability?" Biopharm. Drug. Dispos. vol. 27, 2006, pp. 427-435.
International Search Report and the Written Opinion of the International Searching Authority, issued in corresponding International Application No. PCT/US2019/43856, dated Dec. 3, 2019, 17 pages.
McPherson, "A comparison of salts for the crystallization of macromolecules" (2001), Protein Science (2001), 10:418-422.
Wikipedia, "Buccal administration" Nov. 13, 2016 (Nov. 13, 2016), retrieved on Sep. 27, 2019 from https://en.wikipedia.org/w/Index.php?title=Buccal_administration&oldid=749201264, 2 pages.
Kemp et al., "Epinaphrine: The Drug of Choice for Anaphylaxis—A Statement of the World Allergy Organization", Jul. 2008 (Jul. 2008) WAO Journal, pp. S18-S26.
Britannica Online Encyclopedia, "Malonic acid", Feb. 1, 2007 (Feb. 1, 2007), retrieved on Nov. 12, 2019 from https//www.britannica.com/print/article/360443, 1 page.

\* cited by examiner

*Primary Examiner* — Samantha L Shterengarts
(74) *Attorney, Agent, or Firm* — Rothwell, Figg, Ernst & Manbeck, P.C.

(57) ABSTRACT

Described herein are epinephrine salts, specifically the epinephrine malonate salt; the epinephrine malonate salt in crystalline form; a pharmaceutical composition comprising epinephrine malonate; a sublingual or buccal pharmaceutical composition comprising epinephrine malonate in crystalline form; and a method for treating a patient comprising administering a pharmaceutical composition of epinephrine malonate in crystalline form.

15 Claims, 4 Drawing Sheets

CRYSTALLINE EPINEPHRINE MALONATE SALT

CROSS REFERENCE TO RELATED APPLICATIONS

The present application claims priority to U.S. Provisional Application No. 62/711,936, filed on Jul. 30, 2018, and U.S. Provisional Application No. 62/731,442, filed on Sep. 14, 2018, the disclosures of which are incorporated herein in their entirety by reference.

FIELD OF THE INVENTION

The invention relates to a novel pharmaceutical salt in crystalline form. More particularly, the invention relates to crystalline epinephrine malonate salt; a pharmaceutical composition comprising crystalline epinephrine malonate; and a method for treating a patient comprising administering a pharmaceutical composition of crystalline epinephrine malonate to a patient.

BACKGROUND OF THE INVENTION

Epinephrine has been used for decades for the treatment of anaphylaxis. In 1958, Bose and co-workers studied different epinephrine salts, such as epinephrine citrate, focusing on the pharmacological activity of the epinephrine citrate salt. Bose, et al., *Observations on the pharmacological activity of different salts of adrenaline, morphine and strychnine, Indian J Med Res.* 46(2):193-8 (March 1958). In 1972, John J. Sciarra and co-workers disclosed a method for the preparation of epinephrine maleate, epinephrine malate, and epinephrine fumarate. John J. Sciarra, et al., Synthesis and Formulation of Several Epinephrine Salts as an Aerosol Dosage Form, *Journal of Pharmaceutical Sciences,* 61(2), 219-223 (1972). Other salts studied in the literature include epinephrine hydrochloride and epinephrine bitartrate. T E Peddicord, et al., Stability of high-concentration dopamine hydrochloride, norepinephrine bitartrate, epinephrine hydrochloride, and nitroglycerin in 5% dextrose injection, *Am J Health-Syst Pharm.* 54, 1417-1419 (1997); M M Rawas-Qalaji, et al., Epinephrine for the Treatment of Anaphylaxis: Do All 40 mg Sublingual Epinephrine Tablet Formulations with Similar In Vitro Characteristics Have the Same Bioavailability?, *Biopharm. Drug Dispos.* 27, 427-435 (2006).

SUMMARY OF THE INVENTION

The present invention relates to a novel crystalline epinephrine salt, the epinephrine malonate salt, as well as pharmaceutical compositions comprising said epinephrine salt, methods for preparing said epinephrine salt, and methods for treating patients comprising administering said epinephrine salt to the patient. In a preferred embodiment, the polymorphic crystalline epinephrine malonate has an x-ray powder diffraction pattern identified in FIG. 1.

In certain embodiments, a pharmaceutical composition is provided comprising the epinephrine malonate salt. The pharmaceutical composition can be suitable for oral, rectal, intragastrical, topical, intracranial, intranasal, and parenteral administration. In a preferred embodiment, the pharmaceutical composition can be a sublingual or buccal tablet. The pharmaceutical formulation can comprise a pharmaceutically effective amount of epinephrine malonate salt and one or more pharmaceutically acceptable excipients, including, e.g., a filler (e.g., microcrystalline cellulose) and a disintegrant (e.g., cross-linked polyvinyl polypyrrolidine or a low-substituted hydroxypropyl cellulose). In certain embodiments, the pharmaceutical composition can further include a lubricant (e.g., magnesium stearate) and a glidant (e.g., silicon dioxide). In certain embodiments the pharmaceutical composition can further include a diluent (e.g., mannitol) and/or a pH adjusting agent (e.g., citric acid). The pharmaceutical composition can comprise epinephrine malonate in an amount of 0.3 to 10 mg. The pharmaceutical composition can further comprise a filler in an amount of 20 to 30% by weight and a disintegrant in an amount of 5 to 15% by weight. In certain embodiments, the pharmaceutical composition can disintegrate in less than or equal to 30 seconds.

In certain embodiments, a method for preparing said epinephrine malonate salt is provided. The method can comprise adding malonic acid to a solution of epinephrine base in a solvent (e.g., ethanol). The malonic acid can be added to the solution at a ratio of at least 0.001:1, at least 0.01:1, at least 1:1, at least 2:1, at least 3:1, at least 5:1, at least 10:1, at least 25:1, at least 50:1, at least 100:1, at least 500:1 relative to epinephrine. The malonic acid can be added to the solution at a ratio less than or equal to 100:1, less than or equal to 500:1, less than or equal to 100:1, less than or equal to 75:1, less than or equal to 5:1, less than or equal to 3:1, less than or equal to 2:1, less than or equal to 1:1. In certain embodiments, the malonic acid can be added to the solution at a ratio between 0.01:1 and 3:1. In a preferred embodiment, the malonic acid can be added to the solution at a 1:1 equivalent relative to epinephrine. The method can comprise stirring the solution and precipitating the salt out of solution. The method can further comprise filtering and drying the precipitate.

In certain embodiments, a method for treating a patient is provided. The method comprises administering a pharmaceutically effective amount of epinephrine malonate to a patient in need of such treatment, including, for example, a patient inflicted with anaphylaxis.

BRIEF DESCRIPTION OF THE FIGURES

The accompanying figures, which are incorporated herein and form part of the specification, illustrate various embodiments of the present disclosure and, together with the description, further serve to explain the principles of the disclosure and to enable a person skilled in the pertinent art to make and use the embodiments disclosed herein.

DETAILED DESCRIPTION OF THE INVENTION

Figure 1:
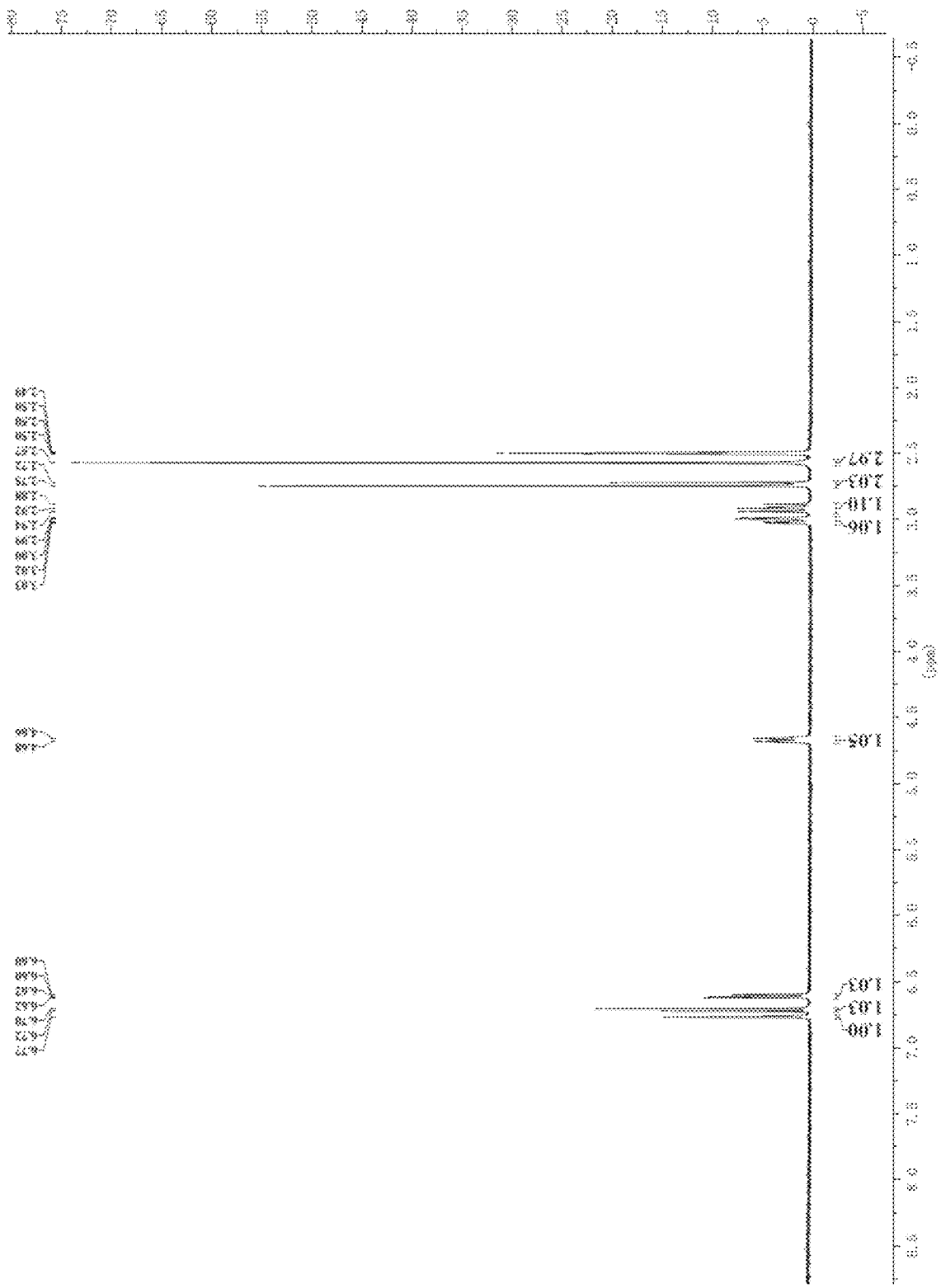
FIG. 1 shows a proton nuclear magnetic resonance (H NMR) spectrum of an epinephrine malonate salt.

The present invention relates generally to a novel crystalline epinephrine salt. A novel salt of epinephrine, epinephrine malonate, has been found that can be obtained in a crystalline form possessing properties desirable for pharmaceutical composition, including for example, sublingual and buccal pharmaceutical compositions.

Before the present invention is described in detail below, it is to be understood that this invention is not limited to the particular methodology, protocols, and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art to which this invention belongs.

The term "about" when used in connection with a numerical value is meant to encompass numerical values within a range having a lower limit that is 5% smaller than the indicated numerical value and having an upper limit that is 5% larger than the indicated numerical value.

As used herein, "treat", "treating" or "treatment" of a disease or disorder means accomplishing one or more of the following: (a) reducing the severity and/or duration of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

A "pharmaceutical composition" according to the invention may be present in the form of a composition, wherein the different active ingredients and diluents and/or carriers are admixed with each other, or may take the form of a combined preparation, where the active ingredients are present in partially or totally distinct form. An example for such a combination or combined preparation is a kit-of-parts.

A "therapeutic amount" or "therapeutically effective amount" is an amount of a therapeutic agent sufficient to achieve the intended purpose. The effective amount of a given therapeutic agent will vary with factors such as the nature of the agent, the route of administration, the size and species of the animal to receive the therapeutic agent, and the purpose of the administration. The effective amount in each individual case may be determined empirically by a skilled artisan according to established methods in the art.

As used herein, the terms "patient" or "subject" most preferably refers to a human being. Also included is any mammal or bird that may benefit from the compounds described herein. Preferably, a "subject" or "patient" is selected from the group consisting of laboratory animals (e.g. mouse or rat), domestic animals (including e.g. guinea pig, rabbit, chicken, turkey, pig, sheep, goat, camel, cow, horse, donkey, cat, or dog), or other primates including chimpanzees.

"Pharmaceutically acceptable" means generally safe for administration to humans or animals. Preferably a pharmaceutically acceptable component is one that has been approved by a regulatory agency of the Federal or a state government or listed in the U.S. Pharmacopeia, published by the United States Pharmacopeial Convention, Inc., Rockville Md., or other generally recognized pharmacopeia for use in animals, and more particularly in humans.

In one embodiment, the present invention provides for epinephrine malonate in a crystalline form having an appearance as a white powder. The epinephrine malonate salt can have a water solubility of 1142.7 mg/mL; a pKa of 5.47; and a partition coefficient (log P) of −3.00. The water solubility of the epinephrine malonate salt in a crystalline form was surprisingly substantially higher than the water solubility of other epinephrine salts. The high water solubility makes the epinephrine malonate salt particularly well suited for transmucosal delivery of the drug. A high bioavailability and rapid delivery of the drug are especially important for epinephrine, which is used to treat anaphylaxis, sometimes in an emergency situation. Additionally, the epinephrine malonate salt is not hygroscopic and can exhibit a favorable stability profile at 7, 14, 30, 60, 90, 120, or 150 days.

The epinephrine malonate salt can be substantially pure. For example, the epinephrine malonate salt can have a purity of greater than or equal to 95%, 96%, 97%, 98%, 99%, 99.5%, 99.6%, 99.7%, 99.8%, or 99.9%.

The epinephrine malonate salt can have a proton nuclear magnetic resonance (H NMR) spectrum as illustrated in FIG. 1.

Figure 2:
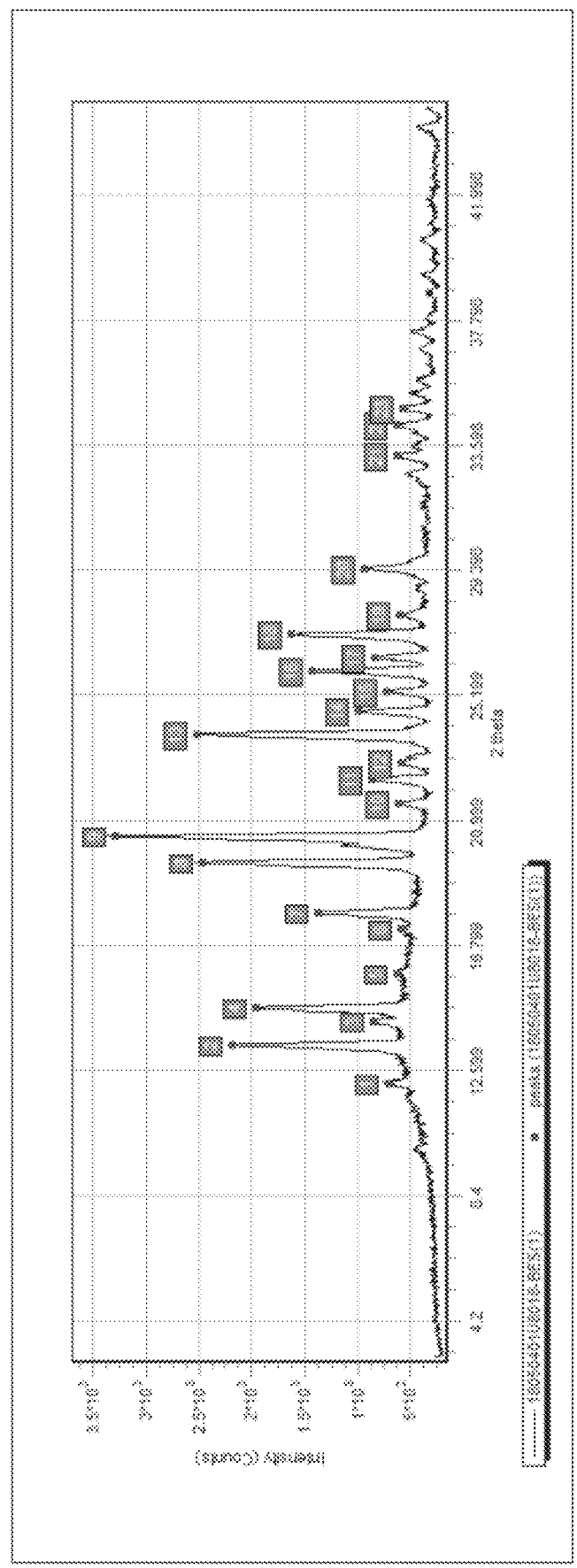
FIG. 2 shows an x-ray powder diffraction (XRPD) spectrum of an epinephrine malonate salt.

The epinephrine malonate salt can have an x-ray powder diffraction (XRPD) spectrum as illustrated in FIG. 2. As illustrated in FIG. 2, the epinephrine malonate salt can be a polymorph characterized by an x-ray powder spectrum (copper, K-alpha-1) having one or more peaks expressed as 2 theta at about 12.1843, 13.4653, 14.2595, 14.6991, 15.8664, 17.3570, 17.9004, 19.5883, 20.4659, 21.5801, 22.3908, 22.9301, 23.8776, 24.6585, 25.3418, 26.0105, 26.4829, 25.3418, 26.0105, 26.4829, 27.2385, 27.8939, 29.4741, 33.2425, 34.2629, 34.8439.

Figure 3:
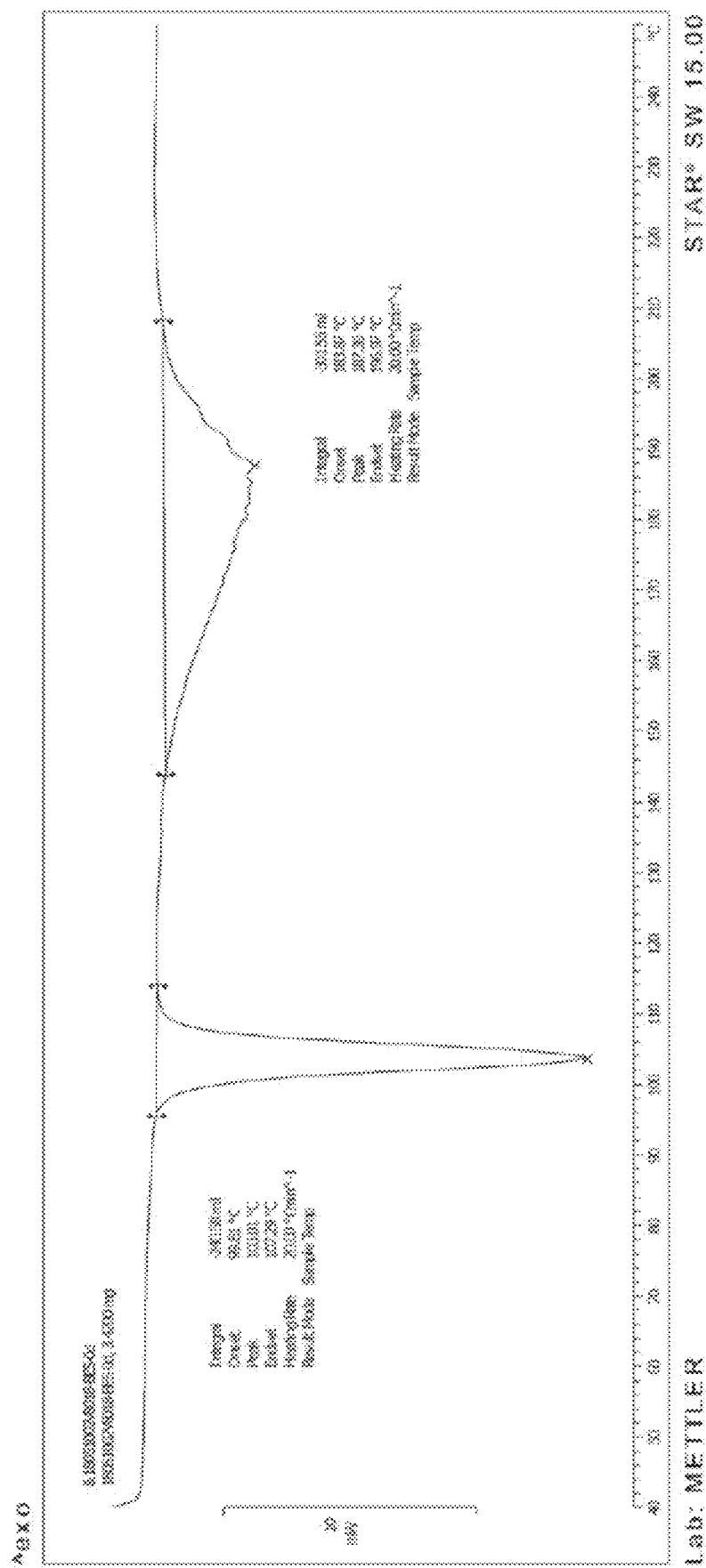
FIG. 3 shows a differential scanning calorimetry (DSC) spectrum of an epinephrine malonate salt.
Figure 4:
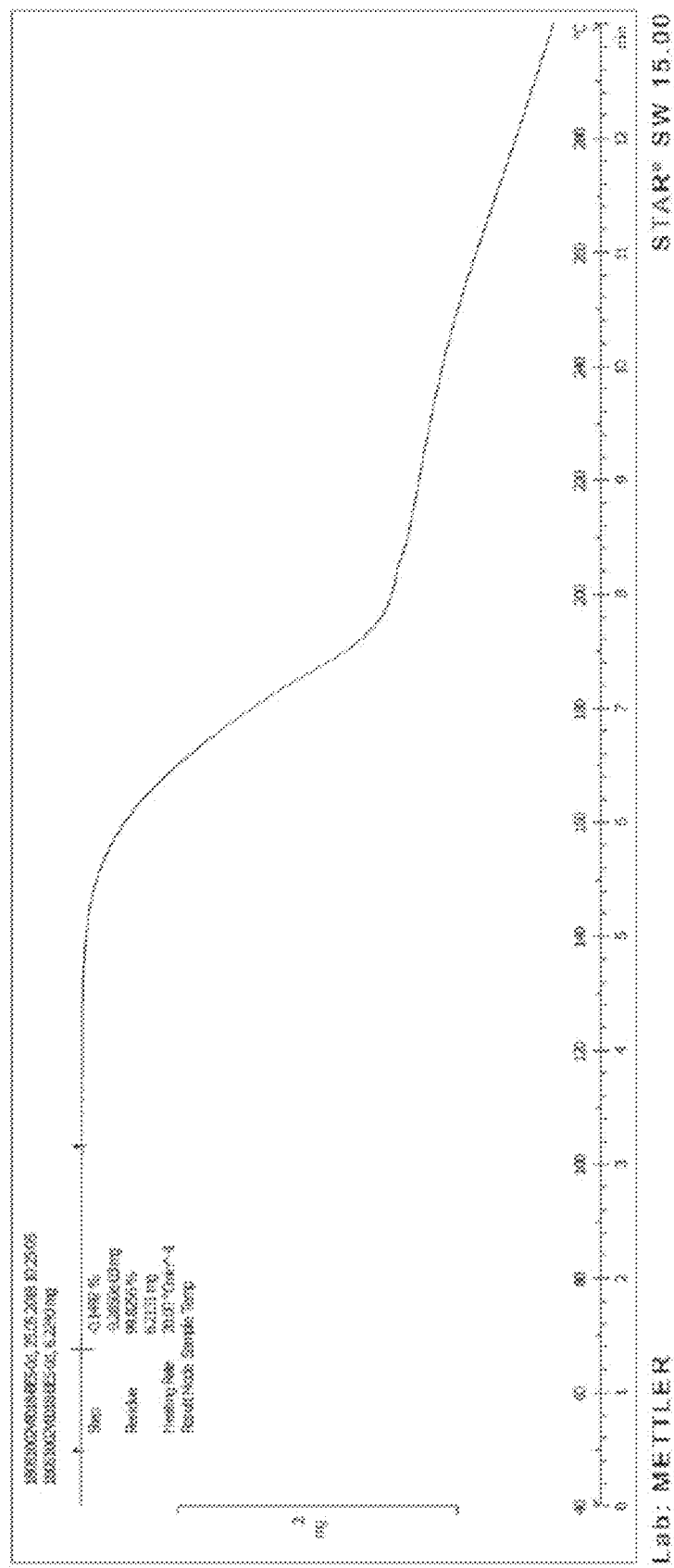
FIG. 4 shows a thermogravimetric analysis of an epinephrine malonate salt.

The epinephrine malonate salt can have a differential scanning calorimetry melting temperature maximum of from about 101° C. to about 106° C., preferably from about 102° C. to 104° C., as illustrated in FIG. 3.

In another embodiment, the present invention provides for a pharmaceutical composition comprising an epinephrine malonate salt. The pharmaceutical composition can be suitable for use in oral, rectal, intragastrical, topical, intracranial, intranasal, and parenteral administration. The pharmaceutical composition can be administered via any pharmaceutically acceptable dosage form, including solid, semi-solid or liquid dosage forms, such as, for example, tablets, suppositories, pills, capsules, powders, liquids, suspensions, or the like, preferably in unit dosage forms suitable for single administration of precise dosages, in immediate release or in sustained or controlled release dosage forms for the prolonged administration of the compound at a predetermined rate. The pharmaceutical composition can include a conventional pharmaceutical carrier or excipient and at least one of the compounds of the present invention and, in addition, may include other medicinal agents, pharmaceutical agents, carriers, adjuvants, etc. The pharmaceutical composition may contain 1 to 95% by weight of the epinephrine malonate salt or more preferably 2 to 50% by weight, 5 to 20% by weight, 10 to 20% by weight, or 5 to 15% by weight of the epinephrine malonate salt. Additionally, the pharmaceutical composition can exhibit a favorable stability profile at 7, 14, 30 days or more.

In preferred embodiments, the pharmaceutical composition is suitable for transmucosal administration in the form of a sublingual or buccal tablet. The pharmaceutical composition can comprise a pharmaceutically effective amount of epinephrine malonate salt. In certain embodiments, the pharmaceutical composition suitable for transmucosal administration in the form of a sublingual or buccal tablet comprises epinephrine free base in an amount of 0.3 to 10 mg. The pharmaceutical composition can further comprise a filler (e.g., microcrystalline cellulose) and a disintegrant (e.g., low-substituted hydroxypropyl cellulose or a cross-linked polyvinyl polypyrrolidone (crospovidone)). In certain embodiments, the pharmaceutical composition can further include a lubricant (e.g., magnesium stearate) and/or a glidant (e.g., silicon dioxide). In certain embodiments, the pharmaceutical composition can further include a diluent (e.g., mannitol). In certain embodiments, the pharmaceutical composition can further include a pH adjusting agent (e.g., citric acid).

In certain embodiments, the filler to disintegrant ratio can be about 9:1, 9.5:0.5, 8:2, 7:3, and 6:4. The pharmaceutical compositions can provide rapid and complete, or substantially complete, disintegration of the buccal or sublingual tablet and can be adjusted to control the disintegration rate of the tablet. For example, the higher the disintegrant ratio, the slower the disintegration of the tablet due to lower water penetration of the tablet through capillary action. In certain embodiments, the buccal or sublingual tablet is capable of substantially or completely disintegrating in less than or equal to 30 seconds. In certain embodiments, the pharmaceutical compositions can comprise one or more fillers, one or more disintegrants, one or more lubricants, and optionally other excipients known in the art. For example, the pharmaceutical composition can include one or more of diluents, binders, glidants, colorants, flavorants, pH adjusting agents, coating materials and the like, as would have been understood by a person of ordinary skill in the art.

In some embodiments of the present invention, the pharmaceutical composition comprises a filler, which is microcrystalline cellulose (e.g., Ceolus®-PH-301 or Ceolus KG 802). In other embodiments, the filler can be one or more of lactose, calcium carbonate, calcium bicarbonate, calcium phosphate, dibasic calcium phosphate, calcium sulfate, calcium silicate, cellulose powders, dextrose, dextrates, dextrans, starches, pregelatinized starches, sucrose, xylitol, lactitol, sorbitol, sodium bicarbonate, sodium chloride, polyethylene glycol, and the like. In certain embodiments, the pharmaceutical composition comprises a filler in an amount of 15-35% by weight, more preferably 20 to 30% by weight or 22 to 27% by weight, or most preferably about 25% by weight.

In some embodiments of the present invention, the pharmaceutical composition comprises a disintegrant, which is cross-linked polyvinyl polypyrrolidone (crospovidone) or a low-substituted hydroxypropyl cellulose. In other embodiments, the disintegrant can be one or more of cross-linked celluloses, such as cross-linked sodium carboxymethyl cellulose, cross-linked carboxymethyl celluloses, or cross-linked croscarmelloses, cross-linked starches such as sodium starch glycolate (e.g., Explotab®), and other cross-linked polymers. In certain embodiments, the pharmaceutical composition comprises a disintigrant in an amount of 2 to 20% by weight, more preferably 5 to 15% by weight or 5 to 10% by weight, or most preferably about 6 to 8% by weight.

In some embodiments of the present invention, the pharmaceutical composition comprises a lubricant, which is magnesium stearate, and/or a glidant, which is silicon dioxide. Lubricants are compounds that prevent, reduce or inhibit adhesion or friction of materials. Glidants are compounds that improve the flowability of the composition. In other embodiments, the lubricants and glidants can be one or more of stearic acid, calcium hydroxide, talc, sodium stearyl fumerate, a hydrocarbon such as mineral oil, or hydrogenated vegetable oil such as hydrogenated soybean oil, higher fatty acids and their alkali-metal and alkaline earth metal salts, such as aluminum, calcium, magnesium, zinc, sodium stearates, glycerol, waxes, Stearowet®, boric acid, sodium benzoate, sodium acetate, sodium chloride, leucine, a polyethylene glycol (e.g., PEG-4000) or a methoxypolyethylene glycol, sodium oleate, sodium benzoate, glyceryl behenate, polyethylene glycol, magnesium or sodium lauryl sulfate, colloidal silica, a starch such as corn starch, silicone oil. In certain embodiments, the pharmaceutical composition comprises a lubricant and/or glidant, individually in an amount of 0.1 to 5% by weight, more preferably 0.5 to 4% by weight, or most preferably about 1 to 3% by weight.

In some embodiments of the present invention, the pharmaceutical composition includes a diluent, which is mannitol. In other embodiments, the diluent can be lactose, starch, sorbitol, dextrose, tricalcium phosphate, calcium phosphate; anhydrous lactose, spray-dried lactose, pregelatinized starch, hydroxypropylmethyl cellulose, hydroxypropylmethyl cellulose acetate stearate, sucrose-based diluents, monobasic calcium sulfate monohydrate, calcium sulfate dehydrate, calcium lactate trihydrate, dextrates, hydrolyzed cereal solids, amylose, powdered cellulose, calcium carbonate, glycine, kaolin, or sodium chloride. In certain embodiments, the pharmaceutical composition comprises a diluent in an amount of 25 to 75% by weight, more preferably 35 to 60% by weight, most preferably 45-55% by weight.

In some embodiments of the present invention, the pharmaceutical composition includes a pH adjusting agent, which is citric acid. In other embodiments, the pH adjusting agent can be boric acid, lactic acid, malic acid, phosphoric acid, sodium phosphate monobasic, or tartaric acid. In certain embodiments, the pharmaceutical composition comprises a diluent in an amount of 0.1 to 3% by weight, more preferably 0.1 to 2% by weight, or most preferably about 0.1 to 1% by weight.

In certain embodiments, the pharmaceutical formulations can be manufactured by using direct compression. As would be understood by a person of ordinary skill in the art, the pharmaceutical formulations can be designed and prepared as set forth in Keith J. Simons et al., *Fast-Disintegrating Sublingual Tablets: Effect of Epinephrine Load on Tablet Characteristics*, AAPS PharmSciTech 7(2):E41 (February 2006), which is incorporated herein by reference.

In other embodiments, the present invention provides for a method for manufacturing an epinephrine malonate salt. The method can comprise adding malonic acid to a solution comprising epinephrine and a solvent. The malonic acid can be added to the solution at a ratio of at least 0.001:1, at least 0.01:1, at least 1:1, at least 2:1, at least 3:1, at least 5:1, at least 10:1, at least 25:1, at least 50:1, at least 100:1, at least 500:1 relative to epinephrine. The malonic acid can be added to the solution at a ratio less than or equal to 100:1, less than or equal to 500:1, less than or equal to 100:1, less than or equal to 75:1, less than or equal to 5:1, less than or equal to 3:1, less than or equal to 2:1, less than or equal to 1:1. In certain embodiments, the malonic acid can be added to the solution at a ratio between 0.01:1 and 3:1. In a preferred embodiment, the malonic acid can be added to the solution at a 1:1 equivalent relative to epinephrine. The method can further comprise stirring the solution. The method can further comprise adding additional solvent to the solution. The method can further comprise stirring the solution. The method can further comprise precipitating the epinephrine salt out of solution. The method can further comprise filtering the precipitate. The method can further comprise drying the precipitate. In the method, the solvent can be an alcohol, ketone, or ester. Exemplary solvents for use with the present invention include methanol, ethanol, n-propanol, iso-propanol, n-butanol, sec-butanol, tert-butanol, n-pentanol, 2-methyl-butanol, 3-methyl-butanol, hexanol, acetone, methyl ethyl ketone, and ethyl acetate. In a preferred embodiment, the solvent is ethanol.

In other embodiments, the present invention provides for a method for treating a patient. The patient may be a patient suffering from an allergic condition, for example anaphylaxis, asthma, or bronchial asthma. The method comprises administering a pharmaceutically effective amount of epinephrine malonate to a patient in need of such treatment, including for example, a patient inflicted with anaphylaxis. The method can comprise administering a buccal or sublingual tablet to the patient afflicted with an allergic condition.

The following examples illustrate certain embodiments of the invention without limitation.

EXAMPLES

While various embodiments have been described herein, it should be understood that they have been presented by way of example only, and not limitation. Thus, the breadth and scope of the present disclosure should not be limited by any of the described exemplary embodiments. Moreover, any combination of the described elements in all possible variations thereof is encompassed by the disclosure unless otherwise indicated herein or otherwise clearly contradicted by context.

Example 1

Preparation of Epinephrine Malonate Salt

Epinephrine malonate salt was formed using the following method. Malonic acid 2.3 g (1.0 eq) was added to a solution of epinephrine 4 g (1.0 eq) in EtOH (8 mL) at room temperature. The reaction mixture turned to a clear solution after vigorously stirring for 30 mins. EtOH (10 mL) was added, and white solid product was precipitated. The mixture was further stirred for 10 hours, filtered and dried in vacuum to afford 5.7 g of the epinephrine malonate salt (as a white powder).

Example 2

Physical and Chemical Properties of Epinephrine Malonate Salt

The physical and chemical properties of the epinephrine malonate salt of Example 1 were assessed and compared to other epinephrine salts.

A. Solubility

The solubility of epinephrine malonate salt was assessed and compared to other epinephrine salts. The tests were conducted using Sartorius balances (Model SQP), a Thermo HPLC (UltiMate 3000 System, UV Wavelength: 205 nm), and Phenomenex Luna columns (5 μm C18 (2), 4.6×250 mm). The column temperature was 40° C. and the autosampler temperature was room temperature. The injection volume was 5 μL.

Mobile Phase A was prepared by weighing 4.0 g tetramethylammonium bisulfate (MERYER, Batch No. 77957139) and 1.1 sodium 1-heptasulfonate (Admas-beta, Batch No. P1343755), and transferring the materials to a flask. 2 mL of 0.1 mol/L EDTA solution (Brand: Sinopharm Chemical Reagent Co., Ltd., Batch No. 20150410) was added to the flask and the volume was adjusted to 950 mL using water. The solution was mixed and adjusted to a pH of 3.5 with 0.1N sodium hydroxide solution (Brand: Enox, Batch No. 20161201). Mobile Phase B was prepared using ethanol. The isocratic elution was used in a proportion of AB of 85/15. The run time was 8 minutes.

A standard solution was used comprising 10 mg of the standard dissolved in 10 mL of water. The test solution solutions were prepared and water was added at 25±2° C. Every 5 minutes, the solution was sonicated for 30 seconds. The dissolution was observed within 30 minutes to make sure the solution was saturated. The solution was filtered through a 0.45 um membrane and the solution was diluted to test. The results of the solubility study are set forth in Table 1.

TABLE 1

| Salt | Solubility (mg/mL) |
|---|---|
| epinephrine malonate | 1142.7 |
| epinephrine bitartrate | 827.0 |
| epinephrine fumarate | 38.9 |
| epinephrine hemi sulfate | 17.7 |
| epinephrine maleate | 82.7 |

B. pH

The pH of epinephrine malonate salt was assessed and compared to other epinephrine salts. The tests were conducted using Sartorius balances (Model SQP) and a pH meter (Brand: INESA, Model No. PHS-3E). 20 mg of the sample was weighed and transferred into a 20 mL volumetric flask with the remainder of the volume comprising water. The solution was mixed. The pH meter was calibrated with pH 4.0 and pH 6.8 standard buffer solutions at 25° C. The results of the analysis are set forth in Table 2.

TABLE 2

| Salt | pH |
|---|---|
| epinephrine malonate | 4.34 |
| epinephrine bitartrate | 3.75 |
| epinephrine fumarate | 3.77 |
| epinephrine hemi sulfate | 7.14 |
| epinephrine maleate | 4.48 |

C. pKa

The pKa of epinephrine malonate salt was assessed and compared to other epinephrine salts. The tests were conducted using Sartorius balances (Model SQP) and a potentiometric titrator (Brand: Methrom, Model No. 905 Titrando). 0.17 g of the sample was weighed and transferred into a 50 mL volumetric flask with the remainder of the volume comprising deionized water. The solution was mixed. The solution was titrated with a 0.1 mol/L NaOH solution using a pH indicator to indicate the end point. The results of the analysis are set forth in Table 3.

TABLE 3

| Salt | pKa |
|---|---|
| epinephrine malonate | 5.47 |
| epinephrine bitartrate | 4.20 |
| epinephrine fumarate | 4.28 |
| epinephrine hemi sulfate | undetermined |
| epinephrine maleate | 6.12 |

D. Partition Coefficient

The partition coefficient (log P) of epinephrine malonate salt was assessed and compared to other epinephrine salts. The tests were conducted using Sartorius balances (Model SQP), a Thermo HPLC (UltiMate 3000 System, UV Wavelength: 205 nm), and Phenomenex Luna columns (5 μm C18 (2), 4.6×250 mm). The column temperature was 40° C. and the autosampler temperature was room temperature. The injection volume was 5 μL.

Mobile Phase A was prepared by weighing 4.0 g tetramethylammonium bisulfate (MERYER, Batch No. 77957139) and 1.1 sodium 1-heptasulfonate (Admas-beta, Batch No. P1343755), and transferring the materials to a flask. 2 mL of 0.1 mol/L EDTA solution (Brand: Sinopharm Chemical Reagent Co., Ltd., Batch No. 20150410) was added to the flask and the volume was adjusted to 950 mL using water. The solution was mixed and adjusted to a pH of 3.5 with 0.1N sodium hydroxide solution (Brand: Enox, Batch No. 20161201). Mobile Phase B was prepared using ethanol. The isocratic elution was used in a proportion of AB of 85/15. The run time was 8 minutes.

A hydrogen disodium phosphate solution was prepared by weighing 7.1 g of hydrogen disodium phosphate (Brand: Sinopharm Chemical Reagent Co., Ltd., Batch No. 20150910). A citric acid solution was prepared by weighing 5.25 g of hydrated citric acid (Brand: General-Reagent, Batch No. 5949-29-1) and dissolving it in 1000 mL of water. A pH 3.47 buffer solution was prepared by adjusting the pH of the hydrogen disodium phosphate solution to 3.47 with the citric acid solution. An n-octanol buffer solution was prepared by mixing 100 mL of n-octanol (Brand: Chinasun Specialty Products Co., Ltd., Batch No. 20160601) and 100 mL of the pH 3.47 buffer solution, vibrated for 24 hours, which sat for an hour to separate the n-octanol phase and the pH 3.47 buffer phase.

10 mg of the sample was dissolved in 10 mL of the saturated n-octanol solution and mixed completely. 10 mL of the saturated pH 3.47 buffer solution was added and vortexed at 3000 r/min for 1 hour. 1 mL of solution was pipetted from the n-octanol and pH 3.47 phase after an hour. A standard solution was prepared containing 1 mg/mL of the standard in diluent. An LOQ solution was prepared from about 0.1% of the standard solution. An n-octanol phase solution was diluted with 1 mL of methanol to test. The pH 3.47 phase solution was injected directly. The partition coefficient was calculated using the following formula: lg $$P = lg\frac{Co}{Cw},$$

wherein Co is the equilibrium concentration of solute in oil phase, and Cw is the equilibrium concentration of solute in water phase. The results of the partition coefficient analysis are reported in Table 4.

TABLE 4

| Salt | LogP |
| --- | --- |
| epinephrine malonate | −3.00 |
| epinephrine bitartrate | −2.95 |
| epinephrine fumarate | −3.00 |
| epinephrine hemi sulfate | N/A |
| epinephrine maleate | −3.01 |

Example 3

Preparation of Pharmaceutical Compositions Comprising Epinephrine Malonate Salt

Pharmaceutical compositions comprising epinephrine malonate salt and other epinephrine salts were prepared. A sublingual tablet was prepared comprising 10 mg epinephrine (calculated by epinephrine base). The composition further comprised microcrystalline cellulose (PH-301) as a filler, low-substituted hydroxypropyl cellulose as a disintegrant, and magnesium stearate as a lubricant. The tablets were prepared by direct compression, using a range of compression forces with the tablet weight around 80 mg.

Example 4

In-Vitro Permeability of Pharmaceutical Compositions

The in-vitro permeability of the pharmaceutical compositions of Example 3 were tested. The tests were conducted using drug transdermal diffusion test instruments (Brand Huanghai, Model No. RJY-6B), Sartorius balances (Model SQP), an INESA pH meter (Model PHS-3E), a Thermo HPLC (UltiMate 3000 System, UV Wavelength: 205 nm), and Phenomenex Luna columns (5 μm C18 (2), 4.6×250 mm). The column temperature was 40° C. and the autosampler temperature was room temperature. The injection volume was 5 μL.

Mobile Phase A was prepared by weighing 4.0 g tetramethylammonium bisulfate (MERYER, Batch No. 77957139) and 1.1 sodium 1-heptasulfonate (Admas-beta, Batch No. P1343755), and transferring the materials to a flask. 2 mL of 0.1 mol/L EDTA solution (Brand: Sinopharm Chemical Reagent Co., Ltd., Batch No. 20150410) was added to the flask and the volume was adjusted to 950 mL using water. The solution was mixed and adjusted to a pH of 3.5 with 0.1N sodium hydroxide solution (Brand: Enox, Batch No. 20161201). Mobile Phase B was prepared using methanol. The isocratic elution was used in a proportion of AB of 85/15. The run time was 10 minutes.

The in vitro diffusion of epinephrine salts were evaluated using Franz cells with an OD of 20 mm and reservoir volume of 7 mL. Dialysis membranes (Spectra/Por® dialysis membranes with 1,000 Da MWCO) were used to simulate sublingual mucous membrane in the vitro permeability tests. The assay content of the active components was detected in receiving pools. A receptor chamber with a magnetic stirrer was filled with phosphate buffer solution (pH 7.4) as the diffusion medium. The water bath was set at 37° C., and water was circulated in the Franz cells.

Each tablet was placed at the center of the donor chamber on the membrane at $T_0$, and 2 mL of the artificial saliva (Brand: Biomart, Brand No. GL0305) was added to facilitate tablet disintegration and dissolution. Aliquots of 1 mL were withdrawn from the receptor chamber at 10, 30, 60, 90, and 120 min. The volumes withdrawn were replenished with fresh medium. Samples were transferred to HPLC vials for HPLC analysis. The results of the in-vitro permeability analysis are reported in Table 5.

TABLE 5

| Epinephrine salt | Diffusion content (%) 120 min |
| --- | --- |
| epinephrine base | 10.5 |
| epinephrine hydrochloride | 44.0 |
| epinephrine bitartrate | 67.8 |
| epinephrine malonate | 57.5 |
| epinephrine fumarate | 54.4 |
| epinephrine hemi sulfate | 42.7 |
| epinephrine maleate | 63.5 |

Example 5

Stability of Pharmaceutical Compositions

The stability of the pharmaceutical compositions of Example 3 were tested. The stability studies were conducted on packaged epinephrine salts at 25° C./RH 60% and 40° C./RH 75% conditions, as well as samples without packaging and exposed to light (4500 Lux) for one month. The appearance, assay content, and related substances were examined at 5, 7, 14 and 30 days.

The assay content was tested using Sartorius balances (Model SQP), an INESA pH meter (Model PHS-3E), a Thermo HPLC (UltiMate 3000 System, UV Wavelength: 205 nm), and Phenomenex Luna columns (5 μm C18 (2), 4.6×250 mm). The column temperature was 40° C., and the autosampler temperature was room temperature. The injection volume was 5 μL.

Mobile Phase A was prepared by weighing 4.0 g tetramethylammonium bisulfate (MERYER, Batch No. 77957139) and 1.1 sodium 1-heptasulfonate (Admas-beta, Batch No. P1343755), and transferring the materials to a flask. 2 mL of 0.1 mol/L EDTA solution (Brand: Sinopharm Chemical Reagent Co., Ltd., Batch No. 20150410) was added to the flask and the volume was adjusted to 950 mL using water. The solution was mixed and adjusted to a pH of 3.5 with 0.1N sodium hydroxide solution (Brand: Enox, Batch No. 20161201). Mobile Phase B was prepared using methanol. The isocratic elution was used in a proportion of AB of 85/15. The run time was 10 minutes.

The assay content was analyzed by dissolving 20 mg of each sample to be examined in 50 mL of Mobile Phase A (0.4 mg/mL) as assay test solution. The sample was used and tested right after it was ready and was protected from light.

The purity was tested using Sartorius balances (Model SQP), an INESA pH meter (Model PHS-3E), a Thermo HPLC (UltiMate 3000 System, UV Wavelength: 205 nm), and PhenomenexSynergi columns (4 μm Polar-RP 80A 250×4.6 mm). The column temperature was 30° C., and the autosampler temperature was room temperature. The injection volume was 5 μL.

Mobile Phase A was prepared by weighing 1.136 g of potassium dihydrogen orthophosphate (Brand: CNW, Batch No. A1040040) and 1.74 g of dipotassium hydrogen orthophosphate (Brand: Ourchem, Batch No. 20160219) and transferring into 1000 mL of water. The pH was adjusted to 3.0±0.05 with orthophosphoric acid (Brand: Ourchem, Batch No. 4112K060). The solution was filtered through a 0.45 μm membrane and degassed. Mobile Phase B was prepared using methanol. The run time was 50 minutes. The gradient set forth in Table 6 was used.

TABLE 6

| Time (min) | Flow (mL/min) | A (%) | C (%) |
|---|---|---|---|
| 0 | 0.5 | 100 | 0 |
| 5 | 0.5 | 100 | 0 |
| 20 | 0.5 | 95 | 5 |
| 35 | 0.5 | 50 | 50 |
| 37 | 0.5 | 100 | 0 |
| 50 | 0.5 | 100 | 0 |

The purity was analyzed by dissolving 10 mg of each sample to be examined in 25 mL of Mobile Phase A (0.4 mg/mL) as purity and related substance test solution. The sample was used and tested right after it was ready and was protected from light. The appearance, assay content, and related substances at 5, 7, 14 and 30 days under different conditions are set forth in Tables 7-9.

TABLE 7

Long Term Stability Study at 25 ± 2° C./60% RH ± 5RH

| Test | 0 days | 5 days | 7 days | 14 days | 30 days |
|---|---|---|---|---|---|
| Epinephrine | | | | | |
| Appearance | Off-white powder | Off-white powder | Off-white powder | Off-white powder | Off-white powder |
| Content (%) | 100.00 | 100.03 | 99.73 | 99.84 | 99.78 |
| Related substance (%) | 0.13 | 0.14 | 0.14 | 0.12 | 0.14 |
| Epinephrine Malonate | | | | | |
| Appearance | Off-white powder | Off-white powder | Off-white powder | Off-white powder | Off-white powder |
| Content (%) | 100.00 | 99.94 | 99.62 | 98.81 | 100.64 |
| Related substance (%) | 0.01 | 0.02 | 0.02 | 0.05 | 0.05 |
| Epinephrine Bitartrate | | | | | |
| Appearance | Off-white powder | Off-white powder | Off-white powder | Off-white powder | Off-white powder |
| Content (%) | 100.00 | 100.05 | 100.83 | 99.82 | 100.33 |
| Related substance (%) | 0.08 | 0.08 | 0.08 | 0.09 | 0.09 |
| Epinephrine Maleate | | | | | |
| Appearance | Off-white powder | Off-white powder | Off-white powder | Off-white powder | Off-white powder |
| Content (%) | 100.00 | 99.50 | 99.97 | 99.43 | 100.69 |
| Related substance (%) | 0.17 | 0.18 | 0.17 | 0.16 | 0.17 |

TABLE 8

Accelerated Stability Study at 40 ± 2° C./75% RH ± 5RH

| Test | 0 days | 5 days | 7 days | 14 days | 30 days |
|---|---|---|---|---|---|
| Epinephrine | | | | | |
| Appearance | Off-white powder | Off-white powder | Off-white powder | Off-white powder | Off-white powder |
| Content (%) | 100.00 | 99.94 | 100.67 | 98.97 | 100.62 |
| Related substance (%) | 0.13 | 0.16 | 0.15 | 0.17 | 0.20 |
| Epinephrine Malonate | | | | | |
| Appearance | Off-white powder | Off-white powder | Off-white powder | Off-white powder | Off-white powder |
| Content (%) | 100.00 | 100.25 | 101.64 | 99.63 | 99.87 |
| Related substance (%) | 0.01 | 0.03 | 0.02 | 0.08 | 0.11 |
| Epinephrine Bitartrate | | | | | |
| Appearance | Off-white powder | Off-white powder | Off-white powder | Off-white powder | Off-white powder |
| Content (%) | 100.00 | 100.43 | 100.84 | 100.17 | 100.96 |
| Related substance (%) | 0.08 | 0.09 | 0.09 | 0.09 | 0.10 |
| Epinephrine Maleate | | | | | |
| Appearance | Off-white powder | Off-white powder | Off-white powder | Off-white powder | Off-white powder |
| Content (%) | 100.00 | 99.30 | 97.76 | 99.24 | 100.19 |
| Related substance (%) | 0.17 | 0.17 | 0.18 | 0.16 | 0.16 |

TABLE 9

Stability Study with Light (4500 Lux) Under Air

| Test | 0 days | 5 days | 7 days | 14 days | 30 days |
|---|---|---|---|---|---|
| Epinephrine | | | | | |
| Appearance | Off-white powder | Off-white powder | Off-white powder | Off-white powder | Off-white powder |
| Content (%) | 100.00 | 100.53 | 99.27 | 99.21 | 98.24 |
| Related substance (%) | 0.13 | 0.15 | 0.18 | 0.18 | 0.21 |
| Epinephrine Malonate | | | | | |
| Appearance | Off-white powder | Off-white powder | Off-white powder | Off-white powder | Off-white powder |
| Content (%) | 100.00 | 99.81 | 98.76 | 99.83 | 100.64 |
| Related substance (%) | 0.01 | 0.03 | 0.03 | 0.06 | 0.04 |
| Epinephrine Bitartrate | | | | | |
| Appearance | Off-white powder | Off-white powder | Off-white powder | Off-white powder | Off-white powder |
| Content (%) | 100.00 | 99.71 | 102.34 | 100.43 | 100.39 |
| Related substance (%) | 0.08 | 0.10 | 0.10 | 0.09 | 0.09 |
| Epinephrine Maleate | | | | | |
| Appearance | Off-white powder | Off-white powder | Off-white powder | Off-white powder | Off-white powder |
| Content (%) | 100.00 | 99.86 | 100.61 | 99.84 | 100.47 |
| Related substance (%) | 0.17 | 0.18 | 0.19 | 0.16 | 0.17 |

Example 6

Extended Stability Study of Epinephrine Malonate with No Humidity

A five month stability study of the epinephrine malonate salt at 30° C. and 40° C. with no humidity was conducted. The epinephrine malonate salt was packaged to avoid light and humidity. The samples were prepared in a brown glass bottle with the outer packing being an aluminum foil bag, and the samples were stored between layers of dessicant silica gels. The appearance, residual material, purity, TGA, and DSC were analyzed each month. The results of the 30° C. stability tests are set forth in Table 10, and the results of the 40° C. stability tests are set forth in Table 11.

TABLE 10

Results of Stability Study at 30° C.

| Time Point (Month) | Appearance | Residual Material (%) | Purity | TGA | DSC |
|---|---|---|---|---|---|
| 0 | Off-white powder | — | 99.96% | 0.32% | Onset: 98.8° C. Offset: 104.25° C. |
| 1 | Off-white powder | 100.31% | 99.96% | 0.60% | Onset: 98.80° C. Offset: 103.99° C. |
| 2 | Off-white powder | 99.42% | 99.96% | 0.19% | Onset: 99.27° C. Offset: 104.47° C. |
| 3 | Off-white powder | 99.44% | 99.96% | 0.90% | Onset: 98.72° C. Offset: 104.23° C. |
| 4 | Off-white powder | 99.31% | 99.73% | 0.69% | Onset: 99.12° C. Offset: 103.62° C. |
| 5 | Off-white powder | 100.22% | 99.96% | 0.51% | Onset: 98.71° C. Offset: 103.92° C. |

TABLE 11

Results of Stability Study at 40° C.

| Time Point (Month) | Appearance | Residual Material (%) | Purity | TGA | DSC |
|---|---|---|---|---|---|
| 0 | Off-white powder | — | 99.96% | 0.32% | Onset: 98.8° C. Offset: 104.25° C. |
| 1 | Off-white powder | 99.59% | 99.97% | 0.16% | Onset: 98.89° C. Offset: 104.41° C. |
| 2 | Off-white powder | 100.11% | 99.96% | 0.13% | Onset: 98.78° C. Offset: 104.05° C. |
| 3 | Off-white powder | 98.97% | 99.96% | 0.51% | Onset: 98.69° C. Offset: 103.33° C. |
| 5 | Off-white powder | 99.68% | 99.96% | 0.46% | Onset: 98.49° C. Offset: 103.83° C. |

Example 7

Stability Study of Epinephrine Malonate at 25° C. in Water

A 120 hour stability study of the epinephrine malonate salt at 25° C. was conducted in water. 20 mg of epinephrine malonate salt was weighed and placed into a 50 mL volumetric flask. The sample was dissolved and diluted to the volume with water and mixed well. The sample was left in an oven at 25° C., and samples were collected at 0 hours, 24 hours, 48 hours, 72 hours, 96 hours, and 120 hours. The diluent (mobile phase) used for the study was prepared by mixing about 1.36 g of potassium dihydrogen orthophosphate and 1.74 g of dipotassium hydrogen orthophosphate in a 1000 mL volumetric flask, and adjusting the pH to 3.0 with orthophosphoric acid. The appearance and purity of the samples were tested. The results of the 25° C. stability test in water are set forth in Table 12.

TABLE 12

| Time Period | Appearance | Purity |
| --- | --- | --- |
| 0 hours | Colorless liquid | 99.97% |
| 24 hours | Colorless liquid | 99.79% |
| 48 hours | Colorless liquid | 99.63% |
| 72 hours | Colorless liquid | 99.51% |
| 96 hours | Colorless liquid | 99.42% |
| 120 hours | Colorless liquid | 99.34% |

Example 8

Degradation Study of Epinephrine Malonate

A degradation study of epinephrine malonate assessing the effect of acid degradation, alkali degradation, oxidation, and thermal degradation (solid and solution) was conducted. The procedure for the various conditions is set forth below.

Standard: 20 mg of sample was weighed and dissolved in a 50 mL volumetric flask, diluted to the required volume with diluents, and mixed well.

Acid Degradation: 20 mg of sample was weighed and placed in a 50 mL volumetric flask. 2 mL of 2.0 mol/L HCl was added to the flask. The flask was placed in a water bath at 40° C. for 7 days.

Alkaline Degradation: 20 mg of sample was weighed and placed in a 50 mL volumetric flask. 2 mL of 0.05 mol/L NaOH was added to the flask. The flask was stored at room temperature for 24 hours.

Oxidation: 20 mg of sample was weighed and placed in a 50 mL volumetric flask. 2 mL of 10% $H_2O_2$ was added to the flask. The flask was placed in a water bath at 40° C. for 44 hours.

Thermal Degradation (solution, 80° C.): 20 mg of sample was weighed and dissolved in a 50 mL volumetric flask, diluted to the required volume with diluents, and mixed well. The flask was placed in a water bath at 80° C. for 46 hours.

Thermal Degradation (solid, 80° C.): 120 mg of sample was placed in an oven at 80° C. for 7 days.

The appearance and purity of the samples were test. The results of the degradation tests are set forth in Table 13.

TABLE 13

| Degradation Type | Appearance | Purity |
| --- | --- | --- |
| Standard | Off-white powder | 99.89% |
| Acid Degradation | Colorless liquid | 91.96% |
| Alkaline Degradation | Brown liquid | 98.68% |
| Oxidation | Colorless liquid | 97.04% |
| Thermal Degradation (solid) | Off-white powder | 99.10% |
| Thermal Degradation (solution) | Colorless liquid | 96.04% |

Example 9

Sublingual Pharmaceutical Composition of Epinephrine Malonate

An epinephrine malonate sublingual tablet was prepared as set forth below. The pharmaceutical composition is set forth in Table 14.

TABLE 14

| Ingredient | Composition per Unit (mg) | % weight/weight |
| --- | --- | --- |
| Epinephrine malonate | 31.36* | 15.68% |
| Microcrystalline cellulose (Ceolus KG 802) | 50 | 25.00% |
| Mannitol (Mannitol Mannogem EZ) | 98.64 | 49.32% |
| Cross-linked polyvinyl polypyrrolidone (crospovidone) | 14 | 7.00% |
| Citric acid (Citric Acid monohydrate) | 1 | 0.50% |
| Silicon dioxide (Cabosil m5p) | 2 | 1.00% |
| Magnesium stearate | 3 | 1.50% |
| Total | 200.00 | 100.00% |

*1 gram of epinephrine malonate salt corresponds to 0.638 g of epinephrine free base. Each tablet comprises 20.0 mg of epinephrine free base.

The tablet was prepared as follows. Epinephrine malonate, microcrystalline cellulose, mannitol, and cross-linked polyvinyl polypyrrolidone were sieved through a 425 micron screen. Citric acid was sieved through an 850 micron screen. The sieved material was transferred to an appropriately sized blending vessel for 500 revolutions. Silicon dioxide was sieved through a 425 micron screen. The silicon dioxide was added to the blending vessel for 125 revolutions. Magnesium stearate was sieved through a 425 micron screen. Magnesium stearate was added to the blending vessel for 125 revolutions. The tablet was blended by compressing a 200 mg dose with between 0.5 KN and 5 KN of force.

Example 10

Stability Testing of Sublingual Pharmaceutical Composition

The stability of the epinephrine malonate sublingual tablet prepared in Example 9 was tested. Tablets were packaged 20 tablets to a bottle, with each bottle containing a single 1.0 gram silica desiccant and sufficient polyester coil to prevent tablet movement. The bottles were capped using a child resistant closure (CRC) with an induction-seal liner and sealed. Bottles were placed in a 40° C. and 25° C. stability chamber. The stability of the samples was assessed in the initial batch (t=0), after 1 week of storage (t=1), and after 4 weeks of storage (t=4). The results of the stability study at 25° C. are set forth in Table 15, and the results of the stability test at 40° C. are set forth in Table 16. An assay of n=10 was performed at each time point.

TABLE 15

Results of Stability Study at 25° C.

| Time | Retention Time | Area | (y − b)/m = x | DF | Epinephrine FBEq mg/tablet | LC (mg) | % LC | Total % Rel | Wt adj. % Assay |
|---|---|---|---|---|---|---|---|---|---|
| t = 0 | 8.289 | 21393253 | 0.401 | 500 | 20.069 | 20 | 100.3 | 0.67 | 101.9 |
| t = 1 | 8.218 | 19343265 | 0.400 | 500 | 20.006 | 20 | 100.0 | 0.69 | 101.7 |
| t = 4 | 8.165 | 3305927 | 0.401 | 500 | 20.055 | 20 | 100.3 | 0.75 | 100.0 |

TABLE 16

Results of Stability Study at 40° C.

| Time | Retention Time | Area | (y − b)/m = x | DF | Epinephrine FBEq mg/tablet | LC (mg) | % LC | Total % Rel | Wt adj. % Assay |
|---|---|---|---|---|---|---|---|---|---|
| t = 0 | 8.289 | 21393253 | 0.401 | 500 | 20.069 | 20 | 100.3 | 0.67 | 101.9 |
| t = 1 | 8.214 | 18861941 | 0.388 | 500 | 19.380 | 20 | 96.9 | 0.66 | 97.5 |
| t = 4 | 8.166 | 3254834 | 0.395 | 500 | 19.743 | 20 | 98.7 | 0.75 | 99.9 |

As illustrated in Tables 15 and 16 herein, the pharmaceutical compositions produced unexpected and surprising stability.

Example 11

Dispersion Testing of Sublingual Pharmaceutical Composition

The rate of dispersion of placebo sublingual tablets similar to those set forth in Example 9 (i.e., the formulation of Example 9 without drug product) was tested after sublingual administration. The placebo tablets had the same composition as the composition set forth in Example 9 with the one difference being the epinephrine malonate salt was replaced with additional diluent (i.e., mannitol). Five human volunteers place one diamond-shaped placebo tablet under their tongue with no water or other liquid added and measured the time required for the tablet to completely disperse. Dispersion was determined by feel and by visual confirmation. Dispersion was complete in all five volunteers within 20 to 25 seconds. As illustrated in this Example 11, the pharmaceutical compositions produced an unexpected and surprising rate of dispersion.

We claim:

1. An epinephrine malonate salt in crystalline form.

2. The epinephrine malonate salt of claim 1, wherein the crystalline form has an x-ray powder diffraction spectrum (copper, K-alpha-1) having one or more peaks expressed as 2 theta at about 12.1843, 13.4653, 14.2595, 14.6991, 15.8664, 17.3570, 17.9004, 19.5883, 20.4659, 21.5801, 22.3908, 22.9301, 23.8776, 24.6585, 25.3418, 26.0105, 26.4829, 25.3418, 26.0105, 26.4829, 27.2385, 27.8939, 29.4741, 33.2425, 34.2629, 34.8439.

3. A pharmaceutical composition comprising epinephrine malonate salt and a pharmaceutically acceptable carrier.

4. The pharmaceutical composition of claim 3, wherein the pharmaceutical composition is suitable for oral, rectal, intragastrical, topical, intracranial, intranasal, and parenteral administration.

5. The pharmaceutical composition of claim 3, wherein the pharmaceutical composition is suitable for sublingual or buccal administration.

6. The pharmaceutical composition of claim 5, wherein the pharmaceutical composition comprises a filler and a disintegrant.

7. The pharmaceutical composition of claim 6, wherein the filler is microcrystalline cellulose and the disintegrant is cross-linked polyvinyl polypyrrolidone.

8. The pharmaceutical composition of claim 7, wherein the filler is present in an amount of 20 to 30% by weight and the disintegrant is present in an amount of 5 to 15% by weight.

9. The pharmaceutical composition of claim 8, further comprising a lubricant and a glidant.

10. The pharmaceutical composition of claim 9, wherein the lubricant is magnesium stearate and the glidant is silicon dioxide.

11. The pharmaceutical composition of claim 10, further comprising a diluent.

12. The pharmaceutical composition of claim 11, wherein the diluent is mannitol.

13. The pharmaceutical composition of claim 12, further comprising citric acid.

14. The pharmaceutical composition of claim 5, wherein the composition comprises an amount of 0.3 to 10 mg of epinephrine free base.

15. The pharmaceutical composition of claim 5, wherein the pharmaceutical composition disintegrates in less than or equal to 30 seconds.

* * * * *